United States Patent [19]

Faict et al.

[11] Patent Number: 5,092,838
[45] Date of Patent: Mar. 3, 1992

[54] HISTIDINE BUFFERED PERITONEAL DIALYSIS SOLUTION

[75] Inventors: Dirk Faict, Assenede B; Francesco Peluso, Heverlee; Patrick Balteau, Saint Georges Sur Meuse, all of Belgium

[73] Assignee: Baxter International Inc., Deerfield, Ill.

[21] Appl. No.: 443,973

[22] Filed: Nov. 30, 1989

[51] Int. Cl.$^5$ .............................................. A61M 1/00
[52] U.S. Cl. ..................................... 604/27; 604/29; 210/647
[58] Field of Search ................................. 604/27–29; 210/647; 435/68.1

[56] References Cited

U.S. PATENT DOCUMENTS

| | | | |
|---|---|---|---|
| 3,764,703 | 10/1973 | Bergström et al. | 514/419 |
| 4,761,237 | 8/1988 | Alexander et al. | 210/647 |
| 4,976,683 | 12/1990 | Gauthier et al. | 604/27 |

*Primary Examiner*—Stephen C. Pellegrino
*Assistant Examiner*—Michael Rafa
*Attorney, Agent, or Firm*—Charles R. Mattenson

[57] ABSTRACT

A peritoneal dialysis solution buffered with L-histidine to a pH of at least 6.5. An apparatus and method for utilizing the solution is also disclosed.

10 Claims, No Drawings

HISTIDINE BUFFERED PERITONEAL DIALYSIS SOLUTION

TECHNICAL FIELD

This invention relates to medical solutions used to extract waste products from a patient's blood and to correct fluid and electrolyte abnormalities in patients with end stage renal disease. More specifically, the invention relates to an amino acid buffered solution for use in peritoneal dialysis.

BACKGROUND

The invention is particularly suited for a blood purification process called peritoneal dialysis (PD) in which a dialyzing solution is placed into a patient's peritoneal cavity and allowed to dwell there for a period of generally four to eight hours. During the course of this dwell period, various waste products, such as urea, will diffuse out of the vascular bed in the peritoneal membrane and into the fluid. Concomitantly, various electrolytes will diffuse from the peritoneal dialysis solution, or dialysate, across the peritoneal membrane and into the blood stream to help restore a proper electrolytic balance.

Most commercially available peritoneal dialysis solutions contain glucose as an osmotic agent to achieve an appropriate osmotic gradient across the membrane and ultrafiltration, the active movement of excess fluid out of the blood and into the PD solution. However, the use of glucose as a component of the dialysate has several disadvantages. Among the disadvantages attendant with the incorporation of glucose into the peritoneal dialysis solution are glucose loading, which may lead, inter alia, to obesity, hyperglycemia, hyperlipidemia.

Another distinct and well known disadvantage of employing glucose in peritoneal dialysis solutions is that at physiologic pH, in the vicinity of 7.4, glucose carmelizes when subjected to sterilizing temperatures of the order of 240° F., decomposing to form 5-hydroxymethyl furfural. To avoid decomposition of the glucose, present practice is to prepare glucose containing dialysate with a pH in the range of 5.0 to 5.9. However, such a relatively low pH has been observed to cause substantial patient discomfort in the form of pain during inflow of the dialysate to the peritoneal cavity.

One of the major causes of change to another form of treatment in patients on peritoneal dialysis is peritonitis. Van Bronswijk, et al. concluded that "the currently available CAPD (continuous ambulatory peritoneal dialysis) solutions are beyond the limits of acid and osmotic tolerance of human phagocytic cells, and may thus compromise the peritoneal defenses of CAPD patients" (van Bronswijk, et al., *Dialysis Fluids and Local Host Resistance in Patients on Continuous Ambulatory Peritoneal Dialysis*, Eur. J. Clin. Microbiol. Infect. Dis., June 1988, p. 368-373). A similar conclusion with respect to pH was drawn by the authors in Harvey, et al., *Effect of Dialysate Fluids on Phagocytosis and Killing by Normal Neutrophils*, J. of Clin. Microbiol., Aug. 1987, p. 1424-1427.

At the onset of inflammation associated with peritonitis in patients treated with PD, a large accumulation of neutrophils occurs in the peritoneal cavity. These neutrophils are primarily responsible for eliminating bacteria from the peritoneal cavity. The bactericidal activity of neutrophils is closely linked to the production of the superoxide radical and therefore impaired formation of superoxide is associated with decreased ability of neutrophils to eliminate bacteria and increased susceptibility to peritonitis. In Ing, et al., *Suppression of Neutrophil Superoxide Production By Conventional Peritoneal Dialysis Solution*, Int. J. of Artif. Organs, vol. 11, no. 5, pp 351-354, it was found that neutrophils exposed to standard acidic PD solutions had a decreased ability to mount a superoxide response while neutrophils exposed to PD solutions having a physiologic pH of 7.4 were able to generate a much larger quantity of superoxide.

Similar results were reported in Duwe, et al., *Effects of Composition of Peritoneal Dialysis Fluid On Chemiluminescence, Phagocytosis and Bactericidal Activity In Vitro*, Infection and Immunity, July 1981, pp 130-135. All three of the tested functions were shown to be strongly inhibited in peripheral blood leukocytes by PD solution with a pH of 5.2.

A further concern with the low pH solutions is acidosis. In fact, in patients with slowed metabolism, such as those with lactic acidosis, alcoholism and diabetes, acidosis may worsen with the extended use of low pH dialysis solutions.

Current commercial and experimental CAPD solutions do not contain a buffer in the physiologic range. As a result, even when adjusted to pH 7, the pH of these solutions rapidly drops to pH 6 or below. U.S. Pat. No. 3,525,686, issued in 1970, recognized the problem of inflow pain due to low pH and, in an attempt to provide a solution with a more physiologic pH, sorbitol, which does not carmelize under conditions of steam sterilization, was substituted for glucose. However, degradation products of glucose are not the only source of acidity. Other materials such as carbon dioxide from the air and products leaching from the container material may lead to lower pH. Furthermore, since the solution does not contain a buffer, minute amounts of acid material will cause a large drop in pH.

U.S. Pat. No. 4,339,433 discloses polyionic polymers as osmotic agents for CAPD solutions. These agents may simultaneously act as buffers. However, these molecules proved to be toxic to the peritoneum and are not available for chronic administration (Mistry, and Gokal, *Alternative Osmotic Agents*, Blood Purification, vol. 7, pp 109-114, 1989).

European Patent application No. 277,868 discloses the use of a glycine based peptide for stabilizing bicarbonate solutions for dialysis. The peptide disclosed also acts as an osmotic agent and therefore as an alternative to glucose.

The use of amino acids in PD solutions was first taught in the preliminary communication on page 812 of the Oct. 12, 1968 issue of the Lancet. In that paper, the only concern being investigated was the extent of amino acid and protein loss during peritoneal dialysis. It was noted that protein loss varied from 20-60 g. and amino acid loss was of the order of an additional 13 g. Patients were given a PD solution which included a 5% concentration of a mixture of amino acids. It was concluded that the addition of a mixture amino acids to PD fluids is a simple way to substantially decrease the fall in serum protein and amino acids in patients undergoing PD.

Solutions containing mixture of amino acids as an alternate osmotic agent to glucose have been investigated and it has been shown that these mixtures can function as alternate osmotic agents. They are absorbed well and therefore can serve as an important source of protein in malnourished patients. However, it must always be borne in mind that one of the primary functions of dialysis is to decrease elevated urea levels in patients with end stage renal disease. Administering amino acids, particularly in concentrations greater than 100 mg/kg body weight/day, may markedly increase blood nitrogen and thereby adversely affect blood urea levels. Clearly, one must be very careful to watch blood urea levels while administering amino acids.

This is a concern also because the amino acid solutions proposed to date as alternatives to glucose solutions have been proven to work only with relatively high concentrations of amino acids, generally of the order of 1 to 2%. Generally, solutions with such high concentrations of amino acids cannot be administered on a chronic basis for all exchanges. Such use leads to often substantial side effects.

Mixtures of aminos acids as buffers have been looked at, but only for organ perfusion solution such as for the heart and kidney. European Patent Application No. 12272 discloses such a protective solution with a buffer system composed of histidine, histidine hydrochloride and tryptophane. U.S. Pat. No. 4,761,237 discloses an improved organ protection solution for the heart and kidney which employs the same histidine, histidine hydrochloride and tryptophane buffer system but with the addition of alpha-ketoglutarate to replace lithium ions and to facilitate the partial reduction of the concentration of the buffer system.

However, it should be borne in mind that these publications looked only at the application of the buffer system in the context of its being employed in an organ perfusion solution. Such a solution has as its primary function the improvement of the organ's resistance to damage caused by the total interruption of blood circulation and the resulting ischemia (lack of oxygen) during reconstructive surgery and transplants and is intended for short-term use only. PD solutions are quite different in that their primary functions are to create diffusion gradients across the peritoneum and induce ultrafiltration and they are intended for long-term use.

SUMMARY OF THE INVENTION

The present invention meets the above concerns by providing a peritoneal dialysis solution buffered to a pH of at least 6.5 by the addition of less than a 1% concentration of amino acids, preferably histidine or derivatives. By administering a solution having a pH much closer to physiologic pH, inflow pain as well as the other problems associated with low pH are substantially reduced if not totally eliminated. Similarly, amino acids have none of the side effects associated with the prior art buffers and in the small amounts employed in the present invention, can be safely administered without substantial risk of undue elevation of blood nitrogen levels.

The amino acid solution of the present invention can be used with all peritoneal dialysis solutions irrespective of the osmotic agent employed. If glycerol or proteins are used as the osmotic agent, the histidine buffer can simply be added to the PD solution. If glucose, related sugars or glucose polymers are employed as the osmotic agent, the solution of the present invention is preferably provided in two part form to allow the portion containing the glucose to be maintained at a lower pH until after sterilization to avoid carmelization. After sterilization, the two portions are mixed to adjust the pH of the final administered peritoneal dialysis solution to be in the range of 6.5 to 7.6.

DESCRIPTION OF THE PREFERRED EMBODIMENTS

The present invention provides a peritoneal dialysis solution buffered at physiologic pH by the addition of amino acids, preferably L-histidine or its optical isomers or derivatives, such as D-histidine, DL-histidine, D-histidine monohydrochloride, DL-histidine monohydrochloride, L-histidine monohydrochloride and histidine oligomers. The amino acids may be employed in small amounts such as 1% or less in solution.

The inventors have found that not only can a standard PD solution be buffered by a single amino acid, but effective buffering can be achieved with quantities of amino acid much smaller than any disclosed or suggested by the prior art. This advance in the PD solution art allows the preparation of glucose and related sugar-based solutions to be prepared and infused into a patient at a pH much closer to physiologic pH. In this way, inflow pain due to low pH is effectively precluded, the problems described above relating to decreased phagocytic activity are effectively negated and, because of the small concentrations of amino acid employed in the preferred embodiment, the side effects commonly associated with prolonged administration of amino acids, including increased blood urea levels, are virtually avoided. Moreover, the inclusion of amino acids, even in such small concentrations, in the dialysate may in fact be beneficial to patients with end stage renal disease as it will have a positive nutritional effect and aid in avoiding protein and amino acid loss.

One of the reasons histidine is preferred from among the available amino acids is its ability to impart substantial buffering effect in the physiologic range, despite the fact that its $pK'_a$ is approximately 6.1, which is outside the normal range one would look to for a buffer to maintain a physiologic pH. Most amino acids do not have a pK' in the range from which one would expect to choose a buffer which would be effective in maintaining a pH of approximately 7.4. Another reason for preferring histidine, its isomers, polymers and derivatives in the present invention is its stability. Unlike other amino acids such as tryptophane, histidine does not require particular protection against light and oxygen to remain stable in solution. Histidine also has a substantial buffering capacity whereas tryptophane has none.

The preferred composition of the present invention will include L-histidine alone as a buffer in an otherwise standard glucose based peritoneal dialysis solution. The L-histidine should preferably be employed in a concentration ranging between 0.01 and 60 millimoles per liter of ready-to-use dialysate and preferably between 1 and 20 millimoles per liter. Such a dialysate may also be prepared from a concentrate or by mixing two or more previously prepared composing solutions. In either case, the initial concentration of histidine should be adjusted to achieve a final, ready-to-use dialysate concentration of amino acid as noted above.

The final amino acid buffered dialysate may be used in peritoneal dialysis with no further special treatment in a manner similar to that employed for previously known dialysis solutions.

While the peritoneal dialysis solution of the present invention may be prepared, sterilized and stored for a reasonable amount of time before use, if the solution is to be sterilized by autoclaving the manufacturer may find it preferable to take a two part approach to preparation. If the solution is to employ glucose or a related molecule as the osmotic agent, the two part approach is to be preferred.

Such an approach would involve preparing a standard glucose PD solution in two parts with the portion containing the glucose or related molecule at a pH in the area of 3.0 to 6.5. The portion containing the amino acid buffer would be prepared in an appropriate concentration in the form of either a concentrate (wet or dry) or a separate solution proportioned to be mixed with the glucose solution to arrive at a the desired composition of finished, ready-to-use dialysate. The two components could then be autoclaved before mixing.

Postponing pH adjustment of the glucose solution to a more physiologic pH until after the heat sterilization step has the distinct advantage of avoiding carmelization of the sugar during sterilization. The components of the final solution may then be mixed immediately after sterilization to achieve the final composition and then stored until use. Alternatively, the sterilized components may be stored until use and mixed immediately prior thereto.

It is this latter procedure which is considered a preferred embodiment in which the components of the final dialysate may be sealed, for example, in separate containers or separate compartments of a single container, joined to one another by any appropriate means for maintaining them in a separate sterile condition and, when mixing is desired, allowing mixing to be achieved without sacrificing sterility. Such an arrangement is preferably achieved by joining the separate containers or compartments with a channel, such as a flexible tube, which contains means, such as a frangible seal, for keeping the components separate until a seal is broken allowing complete mixing while maintaining a closed system to prevent loss of sterility.

The following examples are by way of illustration only and are not intended to limit the scope of the present invention.

EXAMPLE 1

A peritoneal dialysis solution buffered with L-histidine was prepared by mixing two solutions: solution A and solution B. Solution A was made by dissolving 84.08 g/L dextrose in water. Solution B was made by dissolving the following components in water: L-histidine (1.55 g/l); sodium lactate (7.76 g/L)(as a bicarbonate precursor to correct acidosis); $CaCl_2 \cdot 2H_2O$ (0.508 g/L); $MgCl_2 \cdot 6H_2O$ (0.300 g/L); and sodium chloride (11.22 g/L). Solution B was adjusted to pH 7.8 with sodium hydroxide. A PVC bag filled with 1 L of solution A and a PVC bag filled with 1 L of solution B were connected by a tube, obstructed by a frangible part and the entire assembly was sterilized. Two weeks after sterilization, the frangible part was broken and both solutions were mixed. The pH of this final solution was 7.31–7.32.

EXAMPLE 2

Two peritoneal dialysis solutions buffered with L-histidine were made as described in example 1, but 0.779 g and 3.10 g of L-histidine per liter were used respectively in the preparation of solution B. The pH of the final solutions was: 7.13 and 7.43–7.44 respectively.

The invention may be practised other than specifically as described without departing from the spirit or the scope of the claims. For example, the PD solution may be prepared in more than two initial parts or with a combination of isomers and/or derivatives of histidine. Other amino acids may be included, such as for nutritional purposes, if deemed desireable for a particular patient.

That which is claimed is:

1. A method of performing peritoneal dialysis comprising:

providing a first container of solution having a pH of less than 6;

providing a second container of solution including an amino acid buffer being chosen from the group consisting essentially of histidine, its isomers, polymers and derivatives in a concentration such that after mixing said solutions, the final pH of the mixed solution will be greater than 6.5;

providing fluid connection means connecting said first and second containers, said connection means being initially sealed to keep said solutions initially separate, said connections means being unsealable to allow mixing of said solutions;

providing means for delivering the mixture of said solutions to a patient to perform peritoneal dialysis;

unsealing said connections means to open said fluid connection;

mixing said solutions; and delivering said mixed solution via said delivery means.

2. The method of claim 1 wherein the amino acid concentration of said mixed solution is in the range of 0.01 to 60 millimoles per liter.

3. The method of claim 2 wherein the amino acid concentration of said mixed solution is in the range of 1 to 20 millimoles per liter.

4. The method of claim 1 wherein said amino acid buffer is L-histidine.

5. A peritoneal dialysis solution buffered with at least one amino acid to a pH of at least 6.5, said amino acid being chosen from the group consisting essentially of histidine, its isomers, polymers and derivatives.

6. The peritoneal dialysis solution of claim 5 wherein said amino acid is L-histidine.

7. The peritoneal dialysis solution of claim 6 wherein said solution comprises 0.01 to 60 millimoles per liter of said L-histidine.

8. The peritoneal dialysis solution of claim 7 wherein said solution comprises between 1 to 20 millimoles per liter of said L-histidine.

9. The peritoneal dialysis solution of claim 5 wherein said solution comprises 0.01 to 60 millimoles per liter of said amino acid.

10. The peritoneal dialysis solution of claim 9 wherein said solution comprises between 1 to 20 millimoles per liter of said amino acid.

* * * * *